US00PP14622P29

(12) United States Plant Patent
Vandenburg

(10) Patent No.: US PP14,622 P2
(45) Date of Patent: Mar. 23, 2004

(54) CHRYSANTHEMUM PLANT NAMED 'YELLOW CONTACT'

(50) Latin Name: *Chrysanthemum×morifolium*
Varietal Denomination: Yellow Contact

(75) Inventor: Cornelis P. Vandenburg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/452,071

(22) Filed: Jun. 2, 2003

(51) Int. Cl.[7] ..... A01H 5/00
(52) U.S. Cl. ..... Plt./295
(58) Field of Search ..... Plt./295

*Primary Examiner*—Anne Marie Grunberg
(74) *Attorney, Agent, or Firm*—C. A. Whealy

(57) ABSTRACT

A distinct cultivar of Chrysanthemum plant named 'Yellow Contact', characterized by its upright plant habit; freely flowering habit; quill-type decorative-type inflorescences that are about 8.1 cm in diameter; attractive bright yellow; response time about 64 days; dark green foliage; strong peduncles; and excellent postproduction longevity with inflorescences and foliage maintaining good substance and color for about 21 days in an interior environment.

1 Drawing Sheet

Botanical classification/cultivar designation: *Chrysanthemum×morifolium* cultivar Yellow Contact.

BACKGROUND OF THE INVENTION

The present invention relates to a new and distinct cultivar of Chrysanthemum plant, botanically known as *Chrysanthemum×morifolium* and hereinafter referred to by the name 'Yellow Contact'.

The new Chrysanthemum is a naturally-occurring branch mutation of *Chrysanthemum×morifolium* cultivar Contact, disclosed in U.S. Plant Pat. No. 12,734. The new Chrysanthemum was discovered and selected by the Inventor within a population of plants of the cultivar Contact in Madrid, Cundinamarca, Colombia, South America in July, 1998. The selection of this mutation was based on its desirable inflorescence color and good form and substance.

Asexual reproduction of the new Chrysanthemum by terminal cuttings taken in a controlled environment in Madrid, Cundinamarca, Colombia, South America since October, 1998, has shown that the unique features of this new Chrysanthemum are stable and reproduced true to type in successive generations.

SUMMARY OF THE INVENTION

Plants of the cultivar Yellow Contact have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow Contact'. These characteristics in combination distinguish 'Yellow Contact' as a new and distinct cultivar:

1. Upright cut Chrysanthemum that is usually grown as a natural spray.
2. Freely flowering habit, about seven or eight inflorescences per flowering stem.
3. Quill-type decorative-type inflorescences that are about 8.1 cm in diameter.

4. Attractive bright yellow-colored ray florets.
5. Response time about 64 days.
6. Dark green foliage.
7. Strong peduncles.
8. Excellent postproduction longevity with inflorescences and foliage maintaining good substance and color for about 21 days in an interior environment.

Plants of the new Chrysanthemum are most similar to plants of the cultivar Contact. In side-by-side comparisons conducted in Alva, Fla., plants of the new Chrysanthemum differed from plants of the cultivar Contact in the following characteristics:

1. Plants of the new Chrysanthemum flowered later than plants of the cultivar Contact.
2. Plants of the new Chrysanthemum and the cultivar Contact differed in ray floret coloration under low night temperatures. Ray florets of plants of the new Chrysanthemum maintained the bright yellow coloration when exposed to low night temperatures whereas ray florets of the cultivar Contact "bronzed".

BRIEF DESCRIPTION OF THE PHOTOGRAPH

The accompanying colored photograph illustrates the overall appearance of the new Chrysanthemum, showing the colors as true as it is reasonably possible to obtain in colored reproductions of this type. Colors in the photograph may differ slightly from the color values cited in the detailed botanical description which accurately describe the colors of the new Chrysanthemum. The photograph on comprises a side perspective view of a typical flowering stem of 'Yellow Contact' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse.

Two-week old rooted cuttings were planted on Aug. 20, 2002 and received 17 long day/short nights followed by short day/long nights until flowering. Plants were grown as single-stem natural spray cut Chrysanthemums. During the production time, the following environmental conditions were measured: day temperatures, 19 to 24° C.; night temperatures, 4 to 12° C.; and light levels, 3,000 to 5,000 foot candles. Measurements and numerical values represent averages for six to ten typical flowering stems and were taken about ten weeks after the start of short days.

Botanical classification: *Chrysanthemum×morifolium* cultivar Yellow Contact.

Commercial classification: Quill-type decorative-type cut Chrysanthemum.

Parentage: Naturally-occurring branch mutation of the *Chrysanthemum×morifolium* cultivar Contact, disclosed in U.S. Plant Pat. No. 12,017.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous quill-type decorative-type cut flower that is typically grown as a natural spray.

*Flowering stem description.*—Aspect: Erect. Length: About 104 cm. Diameter (natural spray diameter): About 17 cm. Diameter (base of stem): About 5 mm. Internode length: About 4.25 cm. Texture: Pubescent; longitudinally ridged. Color: 146A.

*Foliage description.*—Arrangement: Alternate. Length: About 9 cm. Width: About 6.3 cm. Apex: Mucronate. Base: Truncate. Margin: Palmately lobed; sinuses divergent to parallel. Texture: Upper and lower surfaces pubescent; smooth and leathery; veins prominent on lower surface. Color: Developing and fully expanded foliage, upper surface: 147A. Developing and fully expanded foliage, lower surface: 147B. Venation, upper surface: 147A to 147B. Venation, upper surface: 147B. Petiole: Length: About 2.4 cm. Diameter: About 4 mm. Color: Upper surface: 147B. Lower surface: 147B to 147C.

Flowering description:

*Appearance.*—Decorative-type inflorescence form with quilled-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 64 days later when grown as a natural spray.

*Postproduction longevity.*—In an interior environment, inflorescences and foliage will maintain good color and substance for about 21 days in an interior environment.

*Quantity of inflorescences.*—Freely flowering habit, about seven or eight inflorescences per stem develop.

*Inflorescence size.*—Diameter: About 8.1 cm. Depth (height): About 2.7 cm. Diameter of disc: No disc florets observed. Diameter of receptacle: About 7 mm.

*Inflorescence buds.*—Shape: Oblate. Height: About 6 mm. Diameter: About 7.5 mm. Color: Darker than 146A.

*Ray florets.*—Shape: Tubular; quilled. Length: About 3.9 cm. Width, tube: About 3.25 mm. Width, at apex: About 6 mm. Corolla tube length: About 2.9 mm. Apex: Rounded, acute to emarginate. Base: Fused. Texture: Smooth, satiny, glabrous; longitudinally ridged. Aspect: Initially upright and incurved; when mature, about 45° from vertical. Number of ray florets per inflorescence: About 182 arranged in numerous rows. Color: When opening, upper and lower surfaces: 6A. Fully opened, upper surface: Brighter than 6A. Fully opened, lower surface: 6B to close to 10A.

*Disc florets.*—No disc florets observed.

*Phyllaries.*—Quantity per inflorescence: About 26. Length: About 8 mm. Width: About 2.5 mm. Shape: Lanceolate to deltoid. Apex: Acute. Base: Truncate. Margin: Entire. Texture, upper surface: Smooth, waxy. Texture, lower surface: Pubescent. Color, upper surface: Darker green than 146A. Color, lower surface: 146A.

*Peduncles.*—Length: First peduncle: About 13.25 cm. Fourth peduncle: About 20 cm. Seventh peduncle: About 23.5 cm. Diameter: About 2 mm. Angle: About 30° from vertical. Strength: Strong. Texture: Pubescent. Color: 146A.

*Reproductive organs.*—Androecium: No disc florets observed. Gynoecium: Present on ray florets.

*Seed/fruit.*—Seed and fruit production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. and high temperatures high temperatures of 35° C.

It is claimed:

1. A new and distinct cultivar of Chrysanthemum plant named 'Yellow Contact', as illustrated and described.

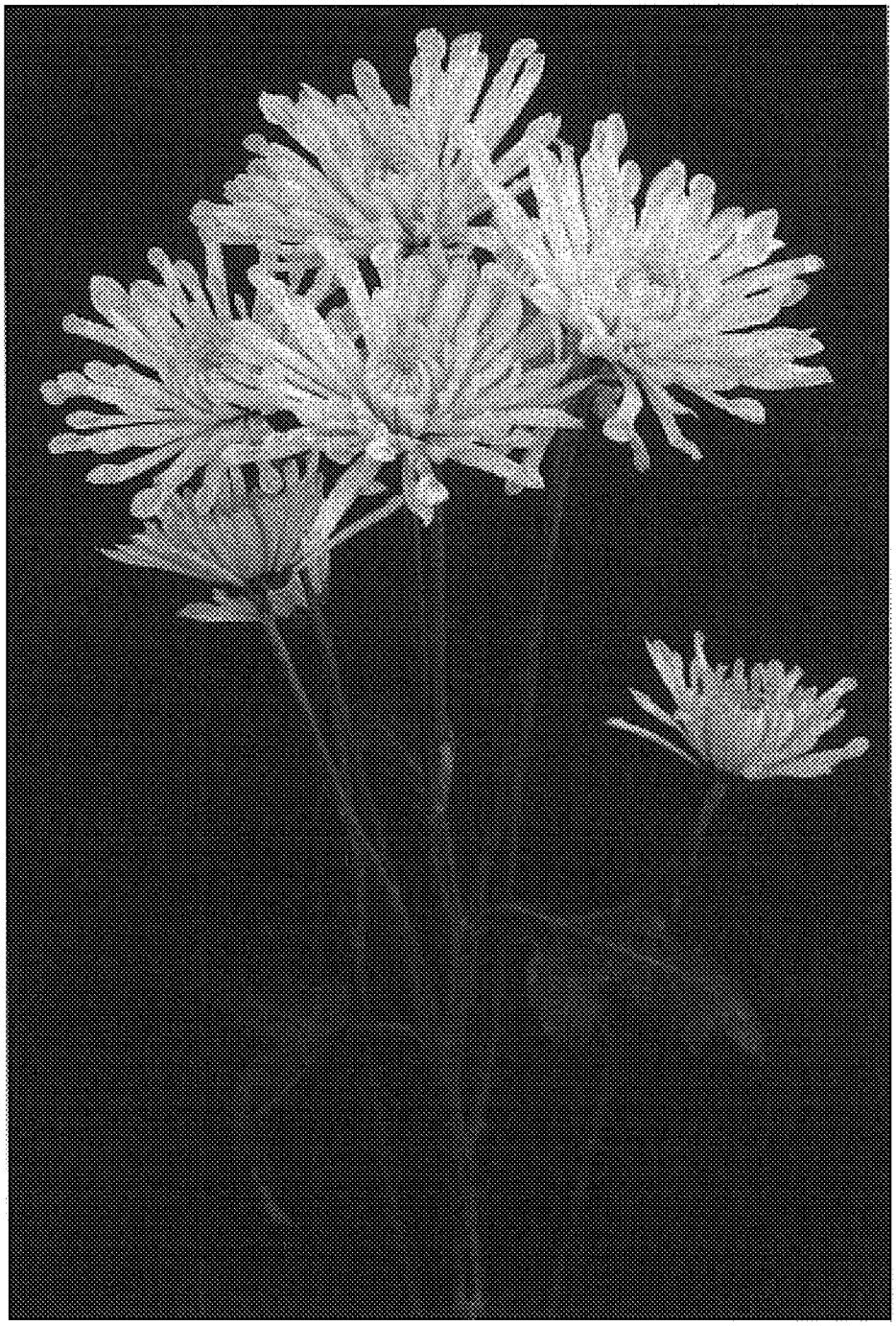

* * * * *